(12) United States Patent (10) Patent No.: US 8,291,337 B2
Gannin et al. (45) Date of Patent: Oct. 16, 2012

(54) INFUSION MANAGEMENT

(75) Inventors: Mary Gannin, Shawnee, KS (US); Lisa Kelly, Overland Park, KS (US); Stephanie Rogers, Kansas City, MO (US); Amanda Buckley, Olathe, KS (US)

(73) Assignee: Cerner Innovation, Inc., Overland Park, KS (US)

( * ) Notice: Subject to any disclaimer, the term of this patent is extended or adjusted under 35 U.S.C. 154(b) by 300 days.

(21) Appl. No.: 12/622,213

(22) Filed: Nov. 19, 2009

(65) Prior Publication Data

US 2011/0072379 A1 Mar. 24, 2011

Related U.S. Application Data

(60) Provisional application No. 61/244,717, filed on Sep. 22, 2009.

(51) Int. Cl.
*G06F 3/048* (2006.01)
*G06F 3/00* (2006.01)
*G06Q 30/00* (2006.01)
*A61M 31/00* (2006.01)

(52) U.S. Cl. ............ 715/771; 715/711; 715/794; 705/3; 604/131

(58) Field of Classification Search .................. 715/771; 705/3; 604/131
See application file for complete search history.

(56) References Cited

U.S. PATENT DOCUMENTS

| | | | |
|---|---|---|---|
| 5,687,717 A * | 11/1997 | Halpern et al. | 600/300 |
| 5,758,095 A * | 5/1998 | Albaum et al. | 705/2 |
| 5,781,442 A * | 7/1998 | Engleson et al. | 700/214 |
| 5,984,893 A * | 11/1999 | Ward | 604/131 |
| 7,879,020 B1 * | 2/2011 | Salinas et al. | 604/503 |
| 7,925,305 B2 * | 4/2011 | Honda | 455/566 |
| 2003/0004758 A1 * | 1/2003 | Luttrell | 705/3 |
| 2003/0069759 A1 * | 4/2003 | Smith | 705/3 |
| 2003/0140928 A1 * | 7/2003 | Bui et al. | 128/898 |
| 2004/0167804 A1 * | 8/2004 | Simpson et al. | 705/3 |
| 2005/0261940 A1 * | 11/2005 | Gay et al. | 705/3 |
| 2006/0100746 A1 * | 5/2006 | Leibner-Druska | 700/282 |
| 2006/0116639 A1 * | 6/2006 | Russell | 604/131 |
| 2006/0229557 A1 * | 10/2006 | Fathallah et al. | 604/131 |
| 2008/0126969 A1 * | 5/2008 | Blomquist | 715/771 |
| 2009/0153058 A1 * | 6/2009 | Feng et al. | 315/76 |
| 2009/0177992 A1 * | 7/2009 | Rubalcaba et al. | 715/771 |
| 2010/0131883 A1 * | 5/2010 | Linthicum et al. | 715/771 |
| 2010/0169120 A1 * | 7/2010 | Herbst et al. | 705/3 |
| 2010/0169121 A1 * | 7/2010 | Herbst et al. | 705/3 |
| 2010/0292645 A1 * | 11/2010 | Hungerford et al. | 604/151 |
| 2011/0137134 A1 * | 6/2011 | Hemmerling et al. | 600/301 |

OTHER PUBLICATIONS

Baxter Launches New Triple-Channel Intravenous Infusion Pump, Sep. 23, 1998. PR Newswire; New York, p. 1.*
Krishnan, et al.; Design of Interoperability-Coupled Safe Infusion Therapy in a Telemetry Setting, May 20, 2009, IFMBE Proceedings (1433-9277), vol. 24.*

* cited by examiner

*Primary Examiner* — Jordany Nunez
(74) *Attorney, Agent, or Firm* — Shook Hardy & Bacon LLP

(57) ABSTRACT

Methods, computer systems and computer readable media for receiving data from infusion pumps in a healthcare setting and displaying the data on a user device are provided. Centralized clinician views are provided to manage individual and multiple patient infusions. Embodiments provide near real-time graphical displays of infusion data to clinicians on separate user devices. In addition, near real-time graphical displays of patient physiologic data is displayed simultaneously to a clinician along with the infusion data.

2 Claims, 12 Drawing Sheets

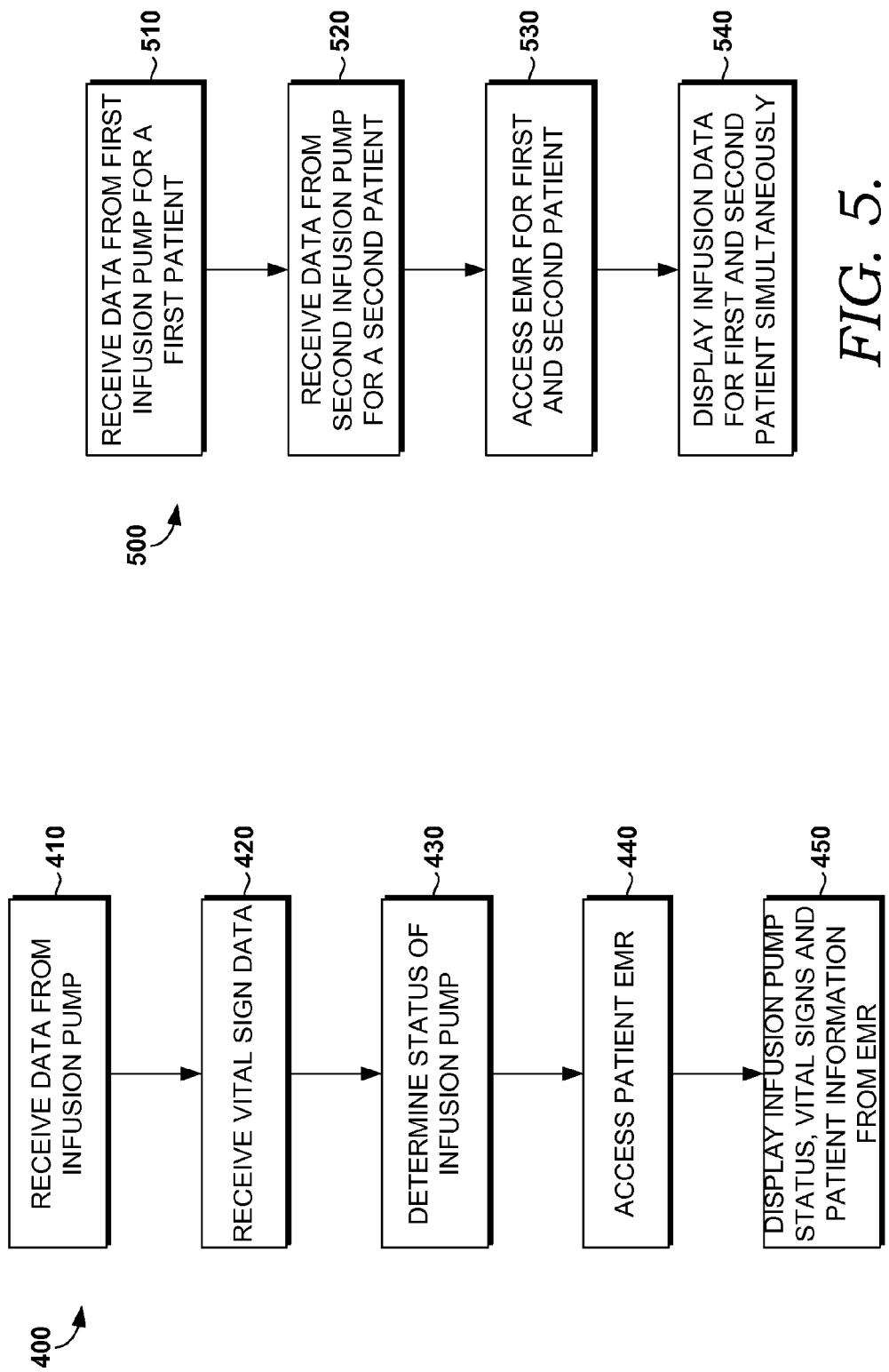

| | PATIENT | ROOM | INGREDIENT | INFUS. TY. | TOTAL | RATE | INFUS. | REMAINING | TIME LEFT | | DISPENSING S... | |
|---|---|---|---|---|---|---|---|---|---|---|---|---|
| ⚠ | COOPER, R | 2154 | DOPAMINE | CONT. | 50ML | 24.75ML/HR | 44.33ML | 5.66 | < 14 MIN | 🔋 | DELIVERED | ▶ SET |
| ⚠ | COOPER, R | 2152 | PROPOFOL | CONT. | 25ML | 24.3ML/HR | 18.53ML | 6.46 | < 16 MIN | 🔋 | DELIVERY IN .... | ▶ SET |
| | ROSS, J | 2152 | NOREPINEPHRINE | CONT. | 16ML | 7.5ML/HR | 13.44ML | 2.55 | < 21 MIN | 🔋 | | ▶ SET |
| | COOPER, R | 2154 | NOREPINEPHRINE | CONT. | 8ML | 7.5ML/HR | 5.43ML | 2.56 | < 21 MIN | 🔋 | DISPENSED | ▶ SET |
| ⚠ | COOPER, R | 2154 | INSULIN | CONT. | 2.85ML | 1.32ML/HR | 2.36ML | 6.48 | < 23 MIN | 🔋 | DISPENSING IN... | ▶ SET |
| | MITCHELL, H | 2147 | DOPAMINE | CONT. | 250ML | 36.75ML/HR | 65.79ML | 184.2 | 5 HR 1MIN | 🔋 | | ▶ SET |
| | JACKSON, L | 2153 | DOPAMINE | CONT. | 250ML | 26.25ML/HR | 47.04ML | 202.95 | 7HR 44MIN | 🔋 | | ▶ SET |
| | LESTER, R | 2151 | DOPAMINE | CONT. | 250ML | 23.34ML/HR | 41.84ML | 208.15 | 8HR 56MIN | 🔋 | | ▶ SET |
| | ROSS, J | 2152 | DOPAMINE | CONT. | 250ML | 20.25ML/HR | 36.28ML | 213.71 | 10HR 34MIN | 🔋 | | ▶ SET |
| | ROBINSON, C | 2154 | PROPOFOL | CONT. | 500ML | 39.6ML/HR | 70.95ML | 429.04 | 10HR 51MIN | 🔋 | | ▶ SET |
| | FRYER, T | 2145 | PROPOFOL | CONT. | 500ML | 35ML/HR | 62.75ML | 437.24 | 12HR 30MIN | 🔋 | | ▶ SET |
| | FRYER, T | 2145 | MILRINONE | CONT. | 40ML | 2ML/HR | 62.75ML | 36.41 | 18HR 13MIN | 🔋 | | ▶ SET |
| | MORRIS, K | 2146 | DOPAMINE | CONT. | 250ML | 10.5ML/HR | 18.82ML | 231.17 | 22HR 2MIN | 🔋 | | ▶ SET |
| | ROBINSON, C | 2154 | MILRINONE | CONT. | 200ML | 6.6ML/HR | 11.83ML | 188.16 | 28HR 31MIN | 🔋 | | ▶ SET |
| ⚠ | LESTER, R | 2151 | NOREPINEPHRINE | CONT. | 250ML | 7.5ML/HR | 13.44ML | 236.55 | 31HR 33MIN | 🔋 | | ▶ SET |
| | MARSHALL, B | 2156 | NOREPINEPHRINE | CONT. | 250ML | 7.5ML/HR | 13.43ML | 236.56 | 31HR 33MIN | 🔋 | | ▶ SET |
| | JONES, T | 2155 | MILRINONE | CONT. | 200ML | 4.88ML/HR | 8.74ML | 191.25 | 39HR 12MIN | 🔋 | | ▶ SET |
| | MORRIS, K | 2146 | MILRINONE | CONT. | 200ML | 4.2ML/HR | 7.53ML | 192.46 | 45HR 50MIN | 🔋 | | ▶ SET |
| | KIRKHOFF, B | 2150 | MILRINONE | CONT. | 200ML | 4.13ML/HR | 7.39ML | 192.6 | 46HR 39MIN | 🔋 | | ▶ SET |
| | FRYER, T | 2145 | INSULIN | CONT. | 100ML | 2ML/HR | 3.58ML | 96.41 | 48HR 13MIN | 🔋 | DISPENSING IN... | ▶ SET |

FIG. 13.

INFUSION MANAGEMENT

CROSS REFERENCE TO RELATED APPLICATIONS

This application claims the benefit of priority to U.S. Provisional Application Ser. No. 61/244,717 filed on Sep. 22, 2009, the entirety of which is hereby incorporated by reference. This application is related to commonly assigned U.S. patent application Ser. No. 12/622,183 entitled "Pharmacy Infusion Management" filed concurrently herewith on the same date.

BACKGROUND

Infusion pumps infuse fluids, medications and/or nutrients into the circulatory system of an individual or patient. The infusions may be intravenous, subcutaneous, arterial, epidural and the like. Infusion pumps can administer injections continuously, intermittently, or upon patient request. Infusion pumps are used by clinicians for patients when more accuracy is needed than with manually adjusted gravitational administration of fluids into a patient's circulatory system. Infusions pumps can be used for infusion of a variety of fluids and medications including, but not limited to anesthesia, chemotherapy, IV drugs, blood transfusions and the like.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

One embodiment of the present invention is directed to one or more computer-readable storage media having computer-executable instructions embodied thereon, that, when executed perform a method for associating an order to a medical device. An identification of a first order for infusion fluid is received. The first order corresponds to a patient. An identification of a first channel of a first infusion pump is received. In response to receiving the identifications of the first order and the first channel of the first infusion pump, the first order and the first channel of the first infusion pump are associated to one another. A continuous data feed from the first infusion pump for the first channel is received.

One embodiment of the present invention is directed to a graphical user interface (GUI) stored on one or more computer-readable media and executable by a computing device. The GUI comprises a first display area configured for displaying infusion data received from a first infusion pump that has been associated with a first order for a patient. The GUI further comprises a second display area configured for displaying vital sign data for the patient received from medical device that has been associated with the patient and a third display area configured for displaying information for the patient received from the electronic medical record for the patient. The first, second and third display areas are displayed simultaneously on a computing device of a clinician that is separate from the first infusion pump and the medical device.

In yet another embodiment of the present invention, a graphical user interface (GUI) stored on one or more computer-readable media and executable by a computing device is provided. The GUI comprises a first display area configured for displaying infusion data received from a first infusion pump for a first patient and a second display area configured for displaying infusion data received from a second infusion pump for a second patient. The infusion data for the first and second infusion pump comprises at least one of current rate of infusion, volume remaining to be infused and alerts. The first and second display areas are displayed simultaneously on a computing device of a clinician that is separate from the first infusion pump and second infusion pumps.

BRIEF DESCRIPTION OF THE DRAWINGS

Embodiments are described in detail below with reference to the attached drawing figures, wherein:

FIGS. 7-13 are screenshots of a graphical user interfaces in accordance with embodiments of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

Embodiments of the present invention are directed methods, computer systems and computer readable media for receiving data from infusion pumps in a healthcare setting and displaying the data on a user device. Centralized clinician views are provided to manage individual and multiple patient infusions. Embodiments provide near real-time graphical displays of infusion data to clinicians on separate user devices. In addition, near real-time graphical displays of patient physiologic data is displayed simultaneously to a clinician along with the infusion data. This allows for clinician verification of the infusion data received to be completed with in context of the patient's hemodynamic and vital sign documentation.

Embodiments of the present invention remove a clinician, such as nurse, from being the integrator of devices and data. Pro-active infusion volume stats and alerts are provided in near real-time to both clinicians and pharmacists increasing nursing and pharmacy efficiency.

Figure 1:
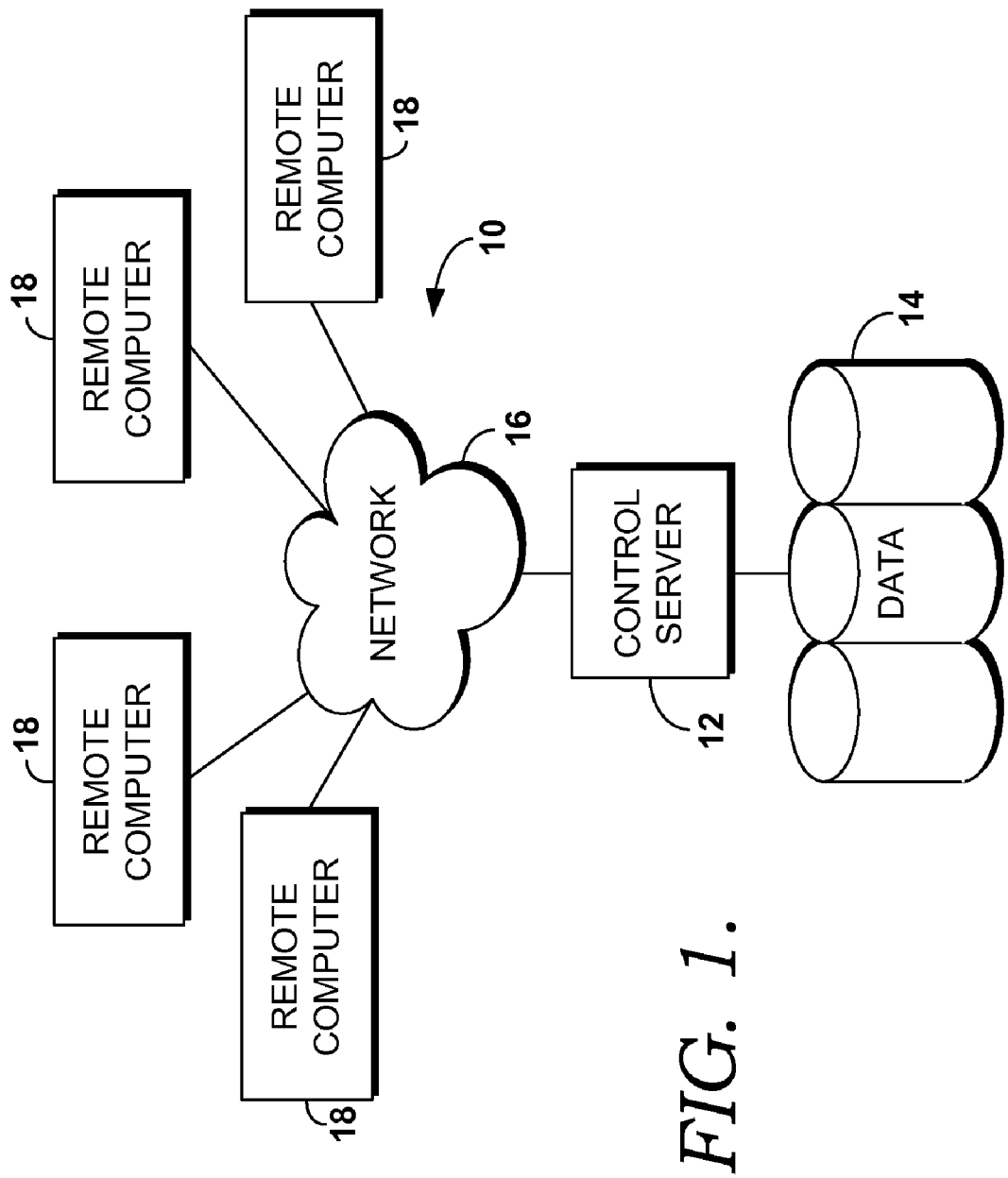
FIG. 1 is a block diagram of an exemplary computing environment suitable to implement embodiments of the present invention.

Having briefly described embodiments of the present invention, an exemplary operating environment suitable for use in implementing embodiments of the present invention is described below. Referring to FIG. 1 an exemplary computing environment (e.g., medical-information computing-system environment) with which embodiments of the present invention may be implemented is illustrated and designated generally as reference numeral 20. The computing environment 20 is merely an example of one suitable computing environment and is not intended to suggest any limitation as to the scope of use or functionality of the invention. Neither should the computing environment 20 be interpreted as having any dependency or requirement relating to any single component or combination of components illustrated therein.

The present invention might be operational with numerous other general purpose or special purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules include routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 20 includes a general purpose computing device in the form of a control server 22. Exemplary components of the control server 22 include a processing unit, internal system memory, and a suitable system bus for coupling various system components, including database cluster 24, with the control server 22. The system bus might be any of several types of bus structures, including a memory bus or memory controller, a peripheral bus, and a local bus, using any of a variety of bus architectures. Exemplary architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 22 typically includes therein, or has access to, a variety of computer-readable media, for instance, database cluster 24. Computer-readable media can be any available media that might be accessed by server 22, and includes volatile and nonvolatile media, as well as, removable and nonremovable media. Computer-readable media might include computer storage media. Computer storage media includes volatile and nonvolatile media, as well as, removable and nonremovable media implemented in any method or technology for storage of information, such as computer-readable instructions, data structures, program modules, or other data. In this regard, computer storage media might include RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 22. Combinations of any of the above also may be included within the scope of computer-readable media.

The computer storage media discussed above and illustrated in FIG. 1, including database cluster 24, provide storage of computer-readable instructions, data structures, program modules, and other data for the control server 22.

The control server 22 might operate in a computer network 26 using logical connections to one or more remote computers 28. Remote computers 28 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians might include a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 28 might also be physically located in nontraditional medical care environments so that the entire healthcare community might be capable of integration on the network. The remote computers 28 might be personal computers, servers, routers, network PCs, peer devices, other common network nodes, or the like and might include some or all of the elements described above in relation to the control server 22. The devices can be personal digital assistants or other like devices.

Exemplary computer networks 26 include local area networks (LANs) and/or wide area networks (WANs). Such networking environments are commonplace in offices, enterprise-wide computer networks, intranets, and the Internet. When utilized in a WAN networking environment, the control server 22 might include a modem or other means for establishing communications over the WAN, such as the Internet. In a networked environment, program modules or portions thereof might be stored in association with the control server 22, the database cluster 24, or any of the remote computers 28. For example, various application programs may reside on the memory associated with any one or more of the remote computers 28. It will be appreciated by those of ordinary skill in the art that the network connections shown are exemplary and other means of establishing a communications link between the computers (e.g., control server 22 and remote computers 28) might be utilized.

In operation, a clinician might enter commands and information into the control server 22 or convey the commands and information to the control server 22 via one or more of the remote computers 28 through input devices, such as a keyboard, a pointing device (commonly referred to as a mouse), a trackball, or a touch pad. Other input devices include microphones, satellite dishes, scanners, or the like. Commands and information might also be sent directly from a remote healthcare device to the control server 22. In addition to a monitor, the control server 22 and/or remote computers 28 might include other peripheral output devices, such as speakers and a printer.

Although many other internal components of the control server 22 and the remote computers 28 are not shown, those of ordinary skill in the art will appreciate that such components and their interconnection are well known. Accordingly, additional details concerning the internal construction of the control server 22 and the remote computers 28 are not further disclosed herein.

Figure 2:
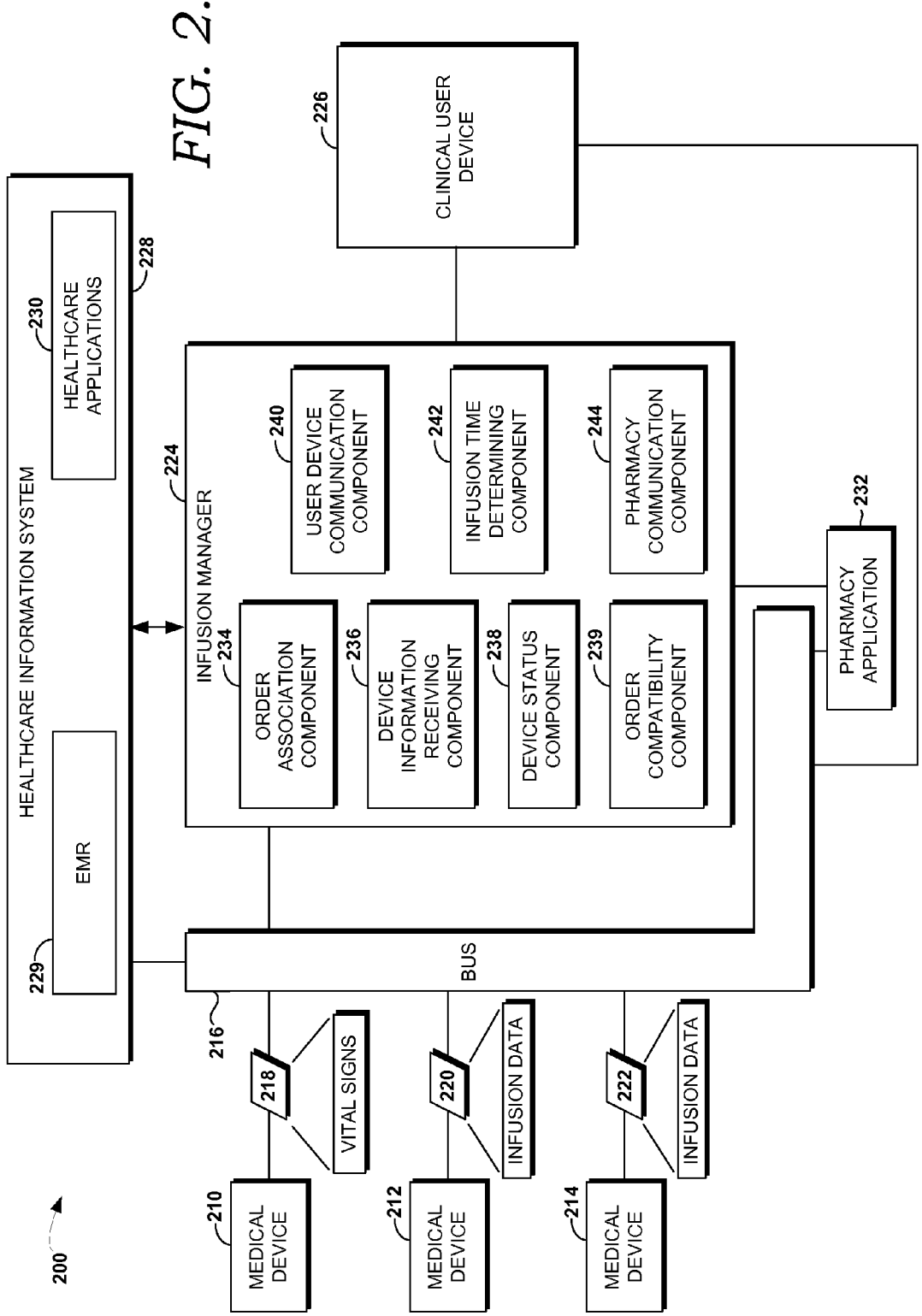
FIG. 2 is an exemplary system architecture suitable to implement embodiments of the present FIGS. 3-6 each include a flow diagram of a method in accordance with an embodiment of the present invention.

Turning now to FIG. 2, a schematic diagram depicts an operating environment, identified generally by reference numeral 200, suitable to practice an embodiment of the present invention. FIG. 2 includes various components that communicate with one another, including medical device 210, infusion pump devices 212 and 214, communication devices 226, bus 216, infusion manager 224, healthcare information system 228 and pharmacy application 232. In one embodiment of the present invention, data generated by a medical device 210 or an infusion pump device 212, and 214 is routed to and managed by infusion manager 224, as opposed to, each medical device 210 and infusion pump device 212 displaying information on the medical device or infusion pump respectively. For example, data 218, 220, and 222 is communicated to bus 216, which might then forward the data to infusion manager 224 to be further processed and routed. Before describing in more detail how these components communicate, each component will be generally described.

In an embodiment of the present invention, medical device 210 might include cardiac monitors, ventilators, balloon pumps, patient beds, sequential-compression devices, electronic security devices, and vital-sign detecting devices. Medical device 210 may generate various data (e.g., measured heart rate) that, as described in more detail below, is communicated to other components (e.g., bus 216) of operating environment 200. Moreover, medical device 210 might also receive information from components of operating environment 200.

In another embodiment of the present invention infusion pumps 212 and 214 infuse fluids, medications and/or nutrients into the circulatory system of an individual or patient. The infusions may be, but are not limited to, intravenous, subcutaneous, arterial, epidural and the like. Infusion pumps can administer injections continuously, intermittently, or upon patient request. Infusion pumps are used by clinicians for patients when more accuracy is needed than with manually adjusted gravitational administration of fluids into a patient's circulatory system. Infusions pumps can be used for infusion of a variety of fluids and medications including, but not limited to anesthesia, chemotherapy, IV drugs, blood transfusions and the like. The fluid, medication and/or nutrients are typically contained in an infusion container, such as an infusion bag. It will be appreciate that any type container may be utilized to hold the infusion fluid, medication and/or nutrients. Infusion pumps 212 and 214 generate various data, including, but not limited to, remaining volume of infusion (e.g., amount remaining in fluid container), rate of infusion (e.g., how fast fluid is being infused), alerts (e.g., air in line, maintenance of pump needed, high backpressure, low infusion, occlusion, or pump stopped). This data is communicated to other components (e.g., bus 216) of operating environment 200. Moreover, infusion pumps 212 and 214 might also receive information from components of operating environment 200.

Healthcare information system 228 includes an integrated system of healthcare-related information that is usable by a healthcare facility to operate and provide patient care. For example, healthcare information system 228 includes an electronic medical record 229 (also referred to herein as "EMR") and a healthcare applications component 230. EMR 229 includes an electronic version of patient records including information for the patient, such as medication and infusion orders, tasks, images, examination reports, testing and lab results, medical history, etc. Healthcare applications component 230 includes information that is input and provided at a patient's point-of-care (e.g., patient bedside) to assist healthcare professionals to provide appropriate care. An exemplary applications component 230 includes a patient order entry component for entering electronic healthcare orders for a patient. In an embodiment of the present invention, healthcare information system 228 receives information from other components, as will be described in more detail below. Moreover, healthcare information system 228 might also provide information that is communicated to other components of operating environment 200.

Communication devices 226 include devices that are used within a healthcare facility to receive, display and send information to a user, such as a clinician. Communication devices 226 also facilitate requests to receive additional information. Exemplary communication devices 226 include personal communication devices, a clinician computer workstation, and an email system. Personal communication devices include devices that are used by an individual to receive and send information, such as an in-house phone, a pager, and a mobile device. Workstations include a remote computer terminal that is used to present information to a user, such as a clinician, and receive input. Workstations might be set up at a nurse's station to or at a patient bedside. Accordingly, in an embodiment of the present invention, communication devices 226 present to users information that is received from other components of operating environment 200. Moreover, communication devices 226 might also receive inputs from a clinician that are communicated to other components of operating environment 200. Communication devices 226 also communicate to other components of operating environment 200 requests to receive additional information. For example, personal communication device 246 might communicate information to infusion manager 224, HIS, 228 EMR 229, pharmacy application 232 and medical devices 210, 212 and 214.

Pharmacy application 232 is an electronic application for receiving medication orders, such as infusion orders, to be filled. An exemplary pharmacy system is Cerner Millennium Pharmnet by Cerner Corporation, Kansas City Mo. Typically orders for medications, fluids and nutrients to be filled by a pharmacist are displayed in the pharmacy or pharmacy IV room. The pharmacist can use this information to drive the pharmacy workflow and make sure the necessary medication orders are filled. In another embodiment, pharmacy application 232 may be an automated pharmacy dispensing system such as Cerner RXStation by Cerner Corporation of Kansas City, Mo. The automated pharmacy system may be an apparatus pre-loaded with medication, fluids and/or nutrients that may be dispensed to fill patient orders.

As previously indicated, and as depicted in FIG. 2, each of medical devices 210, infusion pumps 212 and 214, healthcare information system 228, communication devices 226 and pharmacy application 216 may be in communication with bus 216. Bus 216 generally provides a connection framework for these components by creating and managing all connections, providing a messaging architecture to facilitate an exchange of information between the various components of FIG. 2, and providing general operational and management capabilities for connected devices. In one embodiment, medical device 210, infusion pumps 212 and 214, communication devices 226, healthcare information system 228 and pharmacy application 232 communicate with bus 216 as described in U.S. patent application Ser. No. 12/347,475 (U.S. Pat. App. '475), which is incorporated herein by reference. For example, infusion pumps 212 and 214 might include various different types of infusion pumps that are manufactured by various different vendors. As such, components of FIG. 2 might communicate with bus 216 via a gateway (e.g., device gateway or internal gateway), an adapter, or by any other means described by U.S. Pat. App. '475. In a further embodiment, bus 216 includes those capabilities described in U.S. Pat. App. '475. As indicated in U.S. Pat. App. '475, once data is received (e.g., data 218, 220, 222, and 227) it can be sorted and routed to other applications.

In an embodiment of the present invention, such applications are included in an infusion manager 224. As such, bus 216 might receive information (e.g., data 218, 220, and 222)

and route the data to infusion manager 224. Moreover, bus 216 might receive information from communication devices 226 and route the information to infusion manager 224. In a further embodiment, bus 216 receives information from healthcare information system 228 and routes the information to infusion manager 224. In another embodiment, bus 216 receives information from infusion manager 224 and routes the information to other components. For example, bus 216 routes information from clinician devices 226 to healthcare information system 228.

In an embodiment of the present invention, infusion manager 224 communicates with bus 216 and functions to consolidate and manage information received from the various components of operating environment 200. In this embodiment, instead of components communicating directly with one another, information is routed through and processed by infusion manager 224. Infusion manager 224 allows for consolidation and communication of information from various sources, which may not easily integrated or combinable by direct communication. For example, infusion manager 224 allows for information from infusion pumps 212 and 214 to be packaged with information from medical device 210, healthcare information system 228 and pharmacy application 232 in order to generate and communicate a more information-rich notification to a notification recipient (e.g., personal communication device 246). Moreover, a set of normalized information is more easily sorted and reported than a set of information that organized in alternative formats of various information sources. Alternatively, medical device 210, infusion pumps 212 and 214, pharmacy application 232, clinician user devices 226 and healthcare information system 228 may communicate directly with infusion manager via a network environment.

Infusion manager 224 communicates with bus 216 and functions to document, display and manage infusion information received from infusion pumps 212 and 214. Infusion manager includes order association component 234, device information receiving component 236, device status component 238, order compatibility component 239, user device communication component 240, infusion time determining component 242, and pharmacy communication component 244. While these components are included in the embodiment of FIG. 2, any number of components, either more or less than the illustrated components, may be used to accomplish the purposes of the present invention. Other components and subcomponents are contemplated to be within the scope of the present invention. Furthermore, although depicted as residing on one device, such as a server, it will be appreciated that any number of components and/or subcomponents may reside on any number of computing devices or servers.

Order association component 234 associates the infusion pump and/or pump channel for a patient and an order for a patient in response to receiving an indication that the infusion pump and patient order are to be associated. In one embodiment, if the infusion pump is a multi-channel infusion pump, an order for a patient may be associated with the pump and the particular channel utilized for administration of the ordered medication, fluid and/or nutrient. For example, a first order for a first medication is associated with first channel of a multi-channel pump and a second order for a second, and different, medication for the same patient associated with a second channel of a multi-channel pump.

In one embodiment, identifications of the patient, infusion pump and channel are received. The identifications may be received in a number of ways, including, but not limited to, scanning a barcode associated with the patient, pump and/or channel, entering a name or identification associated with the patient, pump and/or channel or searching an electronically searchable database for a patient, pump and/or channel.

Figure 7:
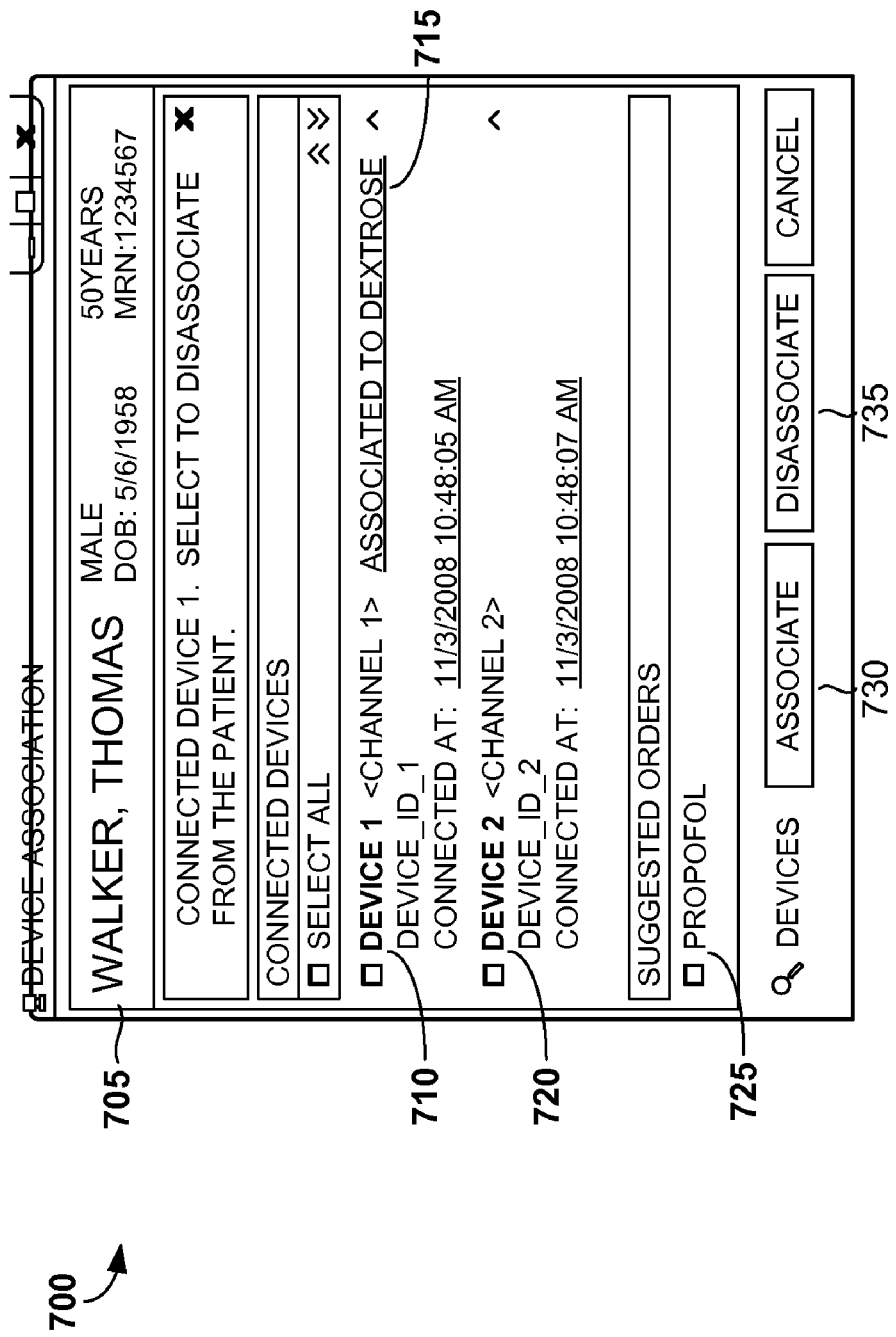

This indication to associate an infusion pump and/or channel and patient order may take many forms. An order is an instruction or request for a procedure, a medication, infusion fluid, nutrients, a laboratory test, an evaluation, a treatment, or a nursing task to be performed for a patient. An explicit association may be available to the user, such as through a selectable button on a graphical user interface displayed on the user device as shown in FIG. 7, described in more detail below. The patient order, infusion pump and/or channel may be associated prior to, simultaneously with of after receiving data from an infusion pump and/or channel. Order association component 234 may suggest orders to associate with one or more infusion pumps and/or channels. For example, order association component 234 may filter patient orders to display only orders to be administered by infusion pump as shown in FIG. 7 which will be discussed in further detail below.

Device information receiving component 236 acquires or receives data from an infusion pump and associated channel that has been associated with a patient and/or order for the patient. The type of data that may be received information regarding volume of fluid infused, volume of fluid remaining to be infused, rate of infusion and alerts. Device information receiving component 236 may also receive data from medical devices other than infusion pumps, such as vital sign and blood pressure monitors. The data is in computerized form and is communicated in electronic form to the BUS and/or event manager without any user intervention. For example, the device would automatically be sent to the BUS and/or infusion manager without a user, such as a nurse or clinician, having to manually key-in or enter any information into a computer system.

In one embodiment, the data received from the infusion pumps and medical devices can be manipulated (e.g., by a clinician) prior to being stored in the patient's EMR. The data may be stored in an application or service such that a user can edit the data prior to the data being transmitted to the patient's EMR. Device information receiving component 236 continually receives data from the associated infusion pumps and medical devices as long as they are associated to the patient and/or patient's order. A continuous feed of data may be fed from the infusion pump and/or medical device to bus 216 and then to infusion manager 224.

Device status determination component 238 determines the status of the device based on data received from an infusion pump. The status may include whether or not a device is connected to the system or if it has lost connectivity, whether a pump is infusing or has been stopped, volume of fluid remaining to be dispensed, rate of infusion and maintenance information. In one embodiment, if the infusion manager 224 does not receive any data from an infusion pump (e.g., such as a heartbeat signal of the device or any other data) it will be determined that the infusion pump has lost connectivity.

In another embodiment, infusion manager 224 may not receive any information about rate or volume remaining but still receives an indication given at a certain interval of time that a particular infusion pump is connected to bus 216. Based on this data, device status determination component 238 determines that the infusion has been stopped but the infusion pump is still connected. Device status determination component 238, if needed, also performs any necessary conversions on the data received from the infusion pump needed to determine the rate of infusion, volume remaining to be infused based on data received from an infusion pump or type of alert needed. In addition, device status determination component 238 can rate the alert information received from the infusion pump and determined by device status determination component 238 by level of severity. The level of severity may be represented by an icon displayed for the alert by user device communication component 240 discussed in further detail below.

Figure 9:
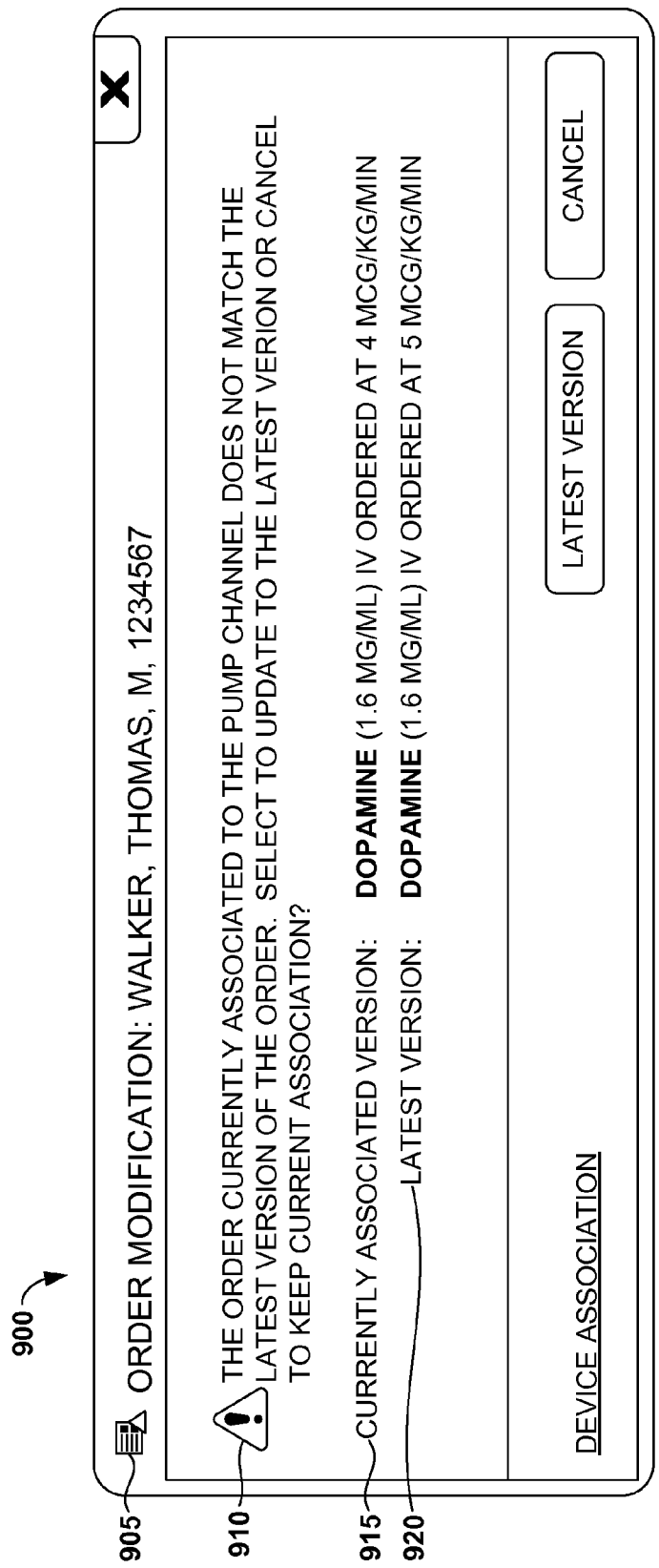

Order compatibility determining component 239 generates an alert that data received from an infusion pump and associated channel does not match the associated order. For example, if the rate of infusion for the associated pump and/or channel received from the data from the pump does not match the rate of the associated order, order compatibility determination component 239 generates an alert notifying a clinician of the discrepancy. In addition, order compatibility determining component 239 can access current electronic orders to be administered by infusion pump for the patient and suggest a more recent version of an order or the closest order that may fit the data being received by the infusion pump as depicted in FIG. 9, which will be discussed in more detail below.

User device communication component 240 displays and communicates data to the user devices 226 and can receive user inputs from a user device 226. The user devices 226 are separate devices from the medical device 210 and infusion pumps 212 and 214. User device communication component 240 can display a variety of information received from an infusion pump in a variety of formats. User device communication component 240 displays an identification of a medical device an associated order for a patient. In addition, user device communication component 240 may display available infusion pumps, pump channels and patient orders to be associated by the order association component 234.

Textual information regarding the rate of infusion of the infusion pump, the volume infused and the volume remaining to be infused may be displayed to a clinician. Textual information regarding the status of the infusion pump generated by device status determination component 238 may be displayed by user device communication component 240. Patient information from the patient's EMR includes details of the order associated with the infusion pump and/or channel, patient identification and demographic information. In addition, user device communication component 240 may provide data received from an infusion pump in a format such that it may be graphed against time on graphical user interface for display to a clinician.

Figure 8:
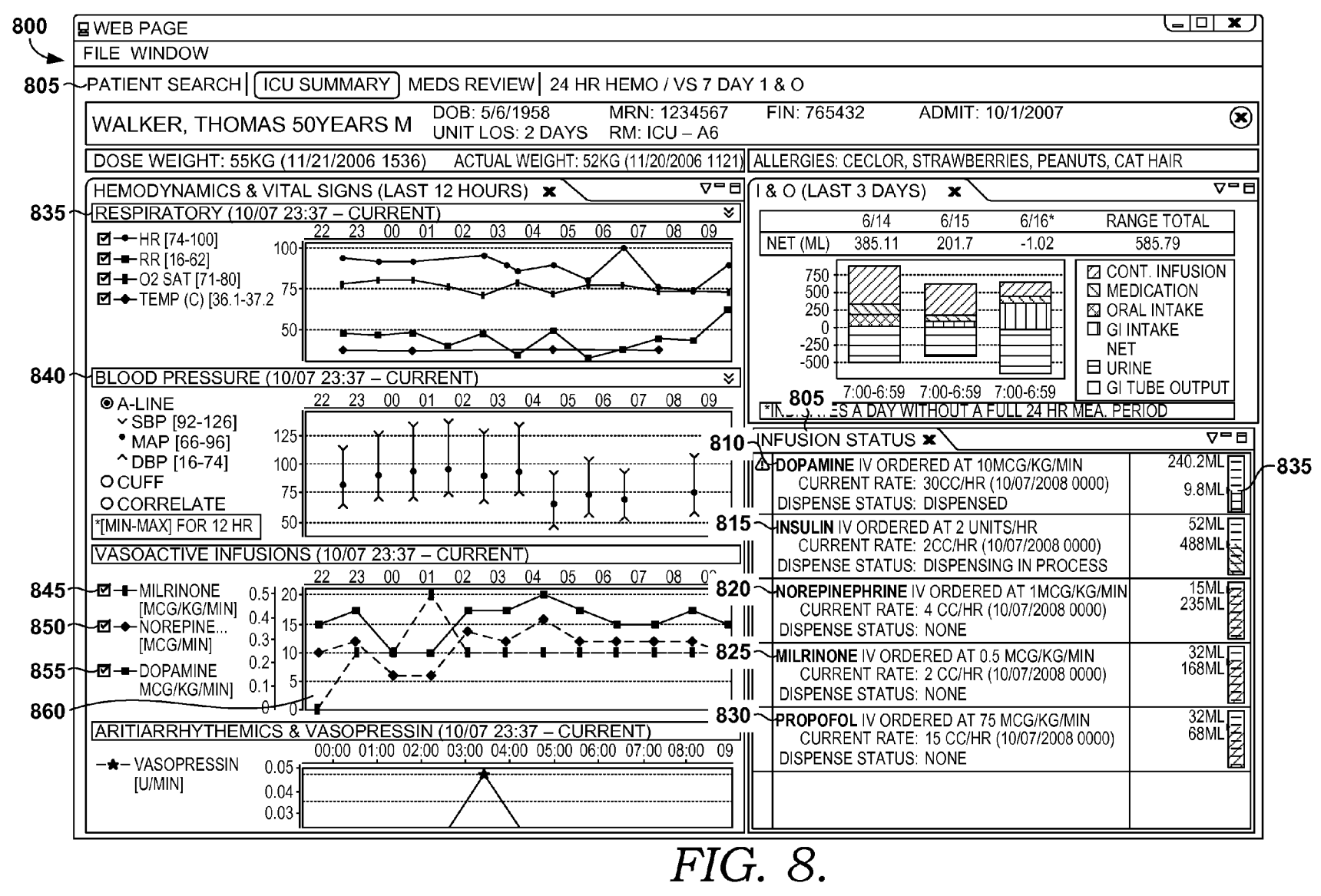
Figure 10:
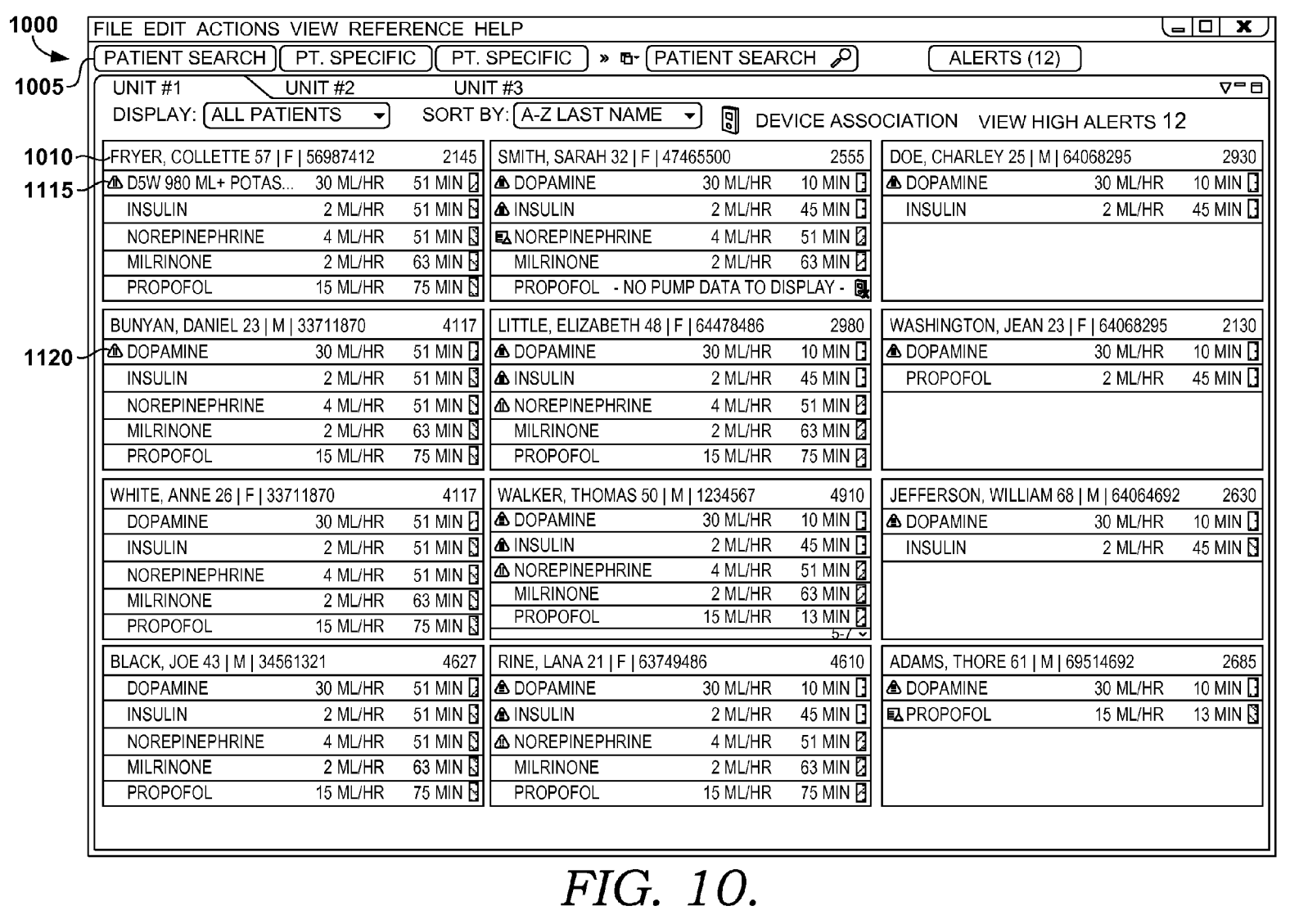

Alerts from the data received from the infusion pump may be displayed along with textual icon and/or color coding indicating the severity of the alert. For example, an alert indicating that there is air in the line for the infusion pump would be indicated as high severity, an alert that an infusion bag had low volume would be indicated as medium severity and a maintenance alert to calibrate the infusion pump would be indicated as low severity. Additional alerts, such as an alert generated by order compatibility determining component 239, alerting a clinician that the order associated with the infusion pump does not match the data being received from the infusion pump may also be displayed. User device communication component 240 may display infusion data for individual patients as shown in FIG. 8 described in more detail below or for multiple patients simultaneously as shown in FIG. 10 also described in more detail below.

User device communication component 240 also provides a user, such as a clinician, with the opportunity to review the data acquired from the infusion pump. The data acquired from the infusion pump and vital signs collected by other medical devices are displayed to the user in a format that allows the user to edit the data received from the infusion pump in context of the patient's vital signs, if desired. Alternatively, the user may authenticate the data as received from the medical device. Once the data received from the infusion pump has been reviewed by a clinician, and once the user has had the opportunity to edit or add any other information, the user may select a button, such as a sign button, that indicates that the data is ready to be transmitted or published to the patient's EMR.

Infusion time determining component 242 determines the time remaining until an infusion needs to be replaced and/or refilled. A variety of information may be utilized to determine the time remaining infusion fluid to be infused. The information utilized may include patient information (patient location, patient identifier), order information (type of infusion, amount, etc.), information from pump (rate, volume infused, volume remaining, alerts) and information from pharmacy that filed the current infusion (e.g., expiration of current infusion). Oftentimes infusion fluids, medications and nutrients have a set expiration time. This information can be obtained from the data from the pharmacy that filled the current infusion. For example, a 50 ml of dopamine may expire in 12 hours.

To calculate the estimated time remaining for until the current infusion fluid runs out, infusion time determining component 242 receives the current rate associated from the infusion pump associated with the patient order or calculates average rate over a period of time (e.g., 24 hours) utilizing the rate data received from the infusion pump associated with the patient order. Additionally, infusion time determining component 242 receives the remaining volume from the infusion pump associated with the patient order. The infusion time determining component 242 then utilizes the rate and volume remaining to determine the estimated time remaining of the current infusion. For example, with reference to FIG. 13, the estimated time remaining for a continuous infusion of dopamine that has 5.66 ml remaining to be infused and a current or average infusion rate of 24.75 ml/hour is calculated as follows:

$$5.66 \text{ ml}/24.75 \text{ ml/hour} = 0.228 \text{ hours}$$

$$0.288 \text{ hours} \times 60 \text{ minutes} = 13.72 \text{ minutes}$$

As such, the estimated time remaining for the infusion is calculated as <14 minutes. In one embodiment, the infusion time determining component 242 compares the estimated time remaining (e.g., <14 minutes) to the expiration time of the current infusion. In this example, the infusion time determining component 242 determines that the estimated time remaining for the infusion will occur before the expiration time of the current infusion and such the estimated time remaining would remain <14 minutes. As such, the pharmacy communication component 244, discussed in more detail below, would notify the pharmacy application 232 that the estimated time remaining of the current infusion is <14 minutes as shown in FIG. 13.

In another embodiment, the infusion time determining component 242 determines that the current infusion will expire in <5 minutes. Thus, the current infusion will expire before the estimated time remaining in the infusion. Thus, pharmacy communication component 244 communicates to the pharmacy application 232 that the current infusion will expire in <5 minutes.

In addition, infusion time determining component 242 determines that the rate of infusion for a patient order is increasing or decreasing. Infusion time determining component 242 utilizes rate information received from an infusion pump over a period of time an average. The infusion time determining component 242 compares the average rate to the current rate to determine if the rate is increasing, decreasing or staying the same. An indication of the increase or decrease in rate can be displayed to a pharmacy application 244 by pharmacy communication component 232.

Infusion time determining component 242 may also filter infusion data for multiple patients to prioritize the pharmacy workflow as shown in FIG. 13. A variety of information may be utilized to prioritize the workflow in the pharmacy. The information utilized may include patient information (patient location, patient identifier), order information (type of infusion, amount, etc.), information from pump (rate, volume infused, volume remaining, alerts), information from pharmacy that filed the current infusion (e.g., expiration of current infusion), known preparation time to prepare an infusion and inventory information.

The infusion time determining component 242 first looks at the time remaining for a current infusion for a patient. For example, infusion time determining component 242 would rank the current infusion for a patient with the least amount of time remaining for the current infusion as the highest priority and a current infusion for the patient with the most amount time remaining the lowest priority. Infusion time determining component 242 would then determine if there is inventory on hand for a current patient infusion. If so, the infusion time determining component 242 may decrease the priority of replacing the current infusion as an infusion from the current inventory will just need to be delivered to the patient. Another factor that may be taken into account is the time to prepare a replacement infusion fluid. For example, a first patient has a current infusion that is estimated to run out in 14 minutes and a second patient has a current infusion that is estimated to run out in 25 minutes. However, the replacement infusion for the first patient will only take two minutes to prepare but the replacement infusion for the second patient will take 20 minutes to prepare. As such, the infusion time determining component 242 will determine to increase the priority of the replacement infusion for the second patient and will change the prioritization rankings accordingly.

Pharmacy communication component 244 displays and communicates infusion pump data to pharmacy application 232. Pharmacy communication component 244 provides near real-time pharmacy awareness of the infusion status of multiple infusion pumps within one or more healthcare facilities.

Pharmacy communication component 244 can display a variety of information received from an infusion pump in a variety of formats to a pharmacy, pharmacy user or an automated pharmacy dispensing system such as Cerner RXStation by Cerner Corporation of Kansas City, Mo. Pharmacy communication component 244 displays patient information such as patient name or ID number along with the patient's location obtained from the patient's EMR 229. Pharmacy communication component 244 displays details regarding the infusion order for the patient such as ingredient, infusion type, and volume to be infused. In addition, pharmacy communication component 244 also displays data received from infusion pumps 212 and 214 including rate of infusion, volume infused, remaining volume to be infused and alerts. Pharmacy communication component 244 also displays calculations performed by infusion time determining component 242 of time left before a current infusion fluid runs out.

Figure 3:
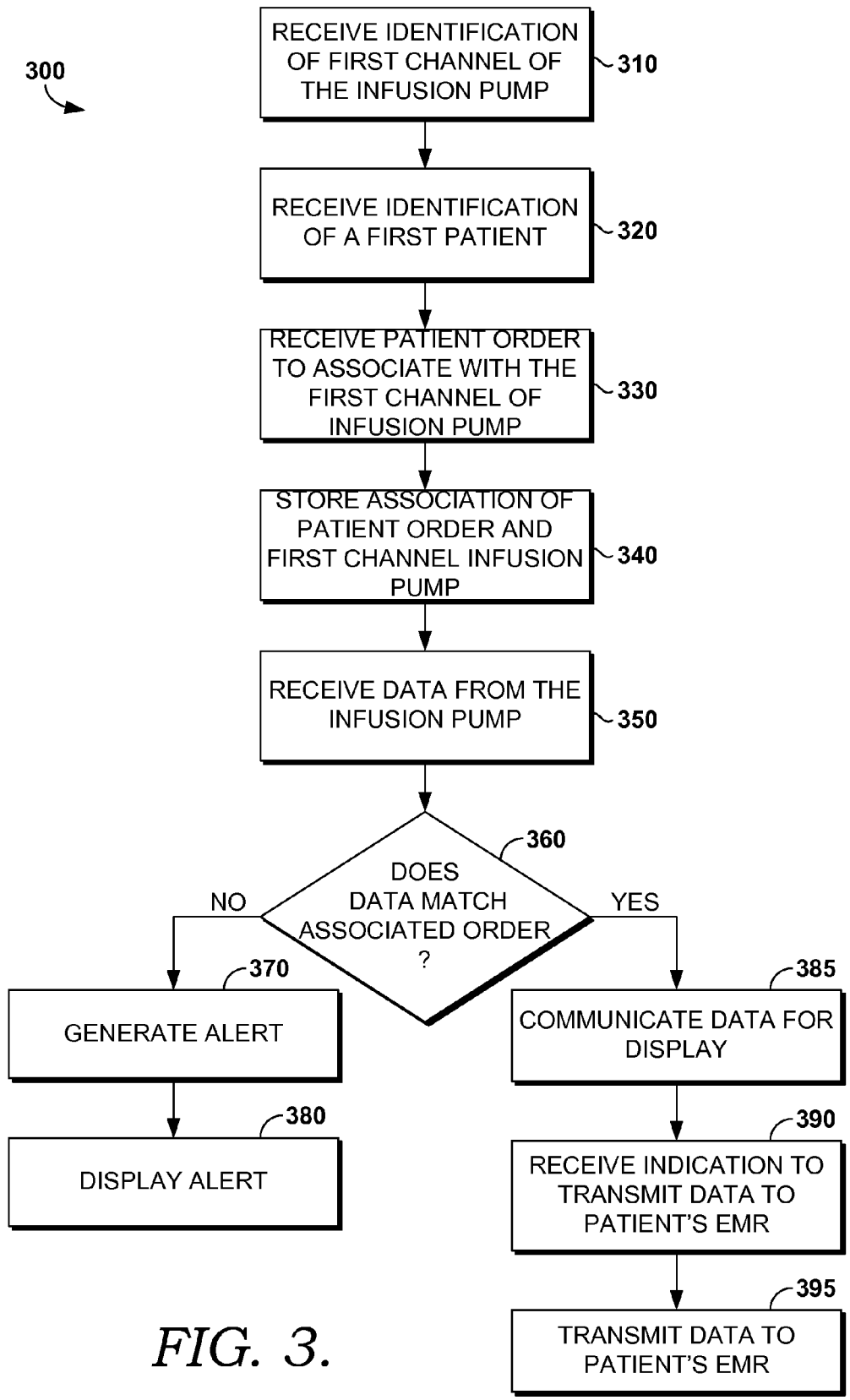

Turning now to FIG. 3, an illustrative flow diagram 300 is shown of a method for associating a patient order and a channel of a multi-channel infusion pump. Initially, an identification of a first infusion pump is received at step 310. An identification of an infusion pump may be received by scanning a bar code corresponding to the infusion pump, entering an identification of the infusion pump into the computing device, or searching for an infusion pump in a database. At step 320, an identification of a patient is received. The identification of the patient may be received in accordance with one of the methods described above, or any other method that allows for identification. At step 330, an identification of an order associated with a patient is received. Again, a patient order may be identified by any of the methods described above. In response to receiving identification of a channel of a multi-channel infusion pump and a patient order, the channel and the patient order are associated with one another and stored at step 340.

A continuous data feed from the infusion pump is received at 350. Data may be received continually from a first time to a second time. In one embodiment, the first time occurred upon initial association of the order to the channel of the infusion pump, and the second time occurred upon termination of the association of the order and a first channel of the infusion pump.

In one embodiment, a second channel of the infusion pump is identified and associated with a second order different from the first order for the patient. Again, this association of the second channel of the infusion pump and the second order is stored for the patient. As such, each channel of an infusion pump may be associated with a different order for the patient.

At step 360, it is determined whether the data received from the infusion pump for the first channel matches that of the first associated order. If the data does not match at step 360, an alert is generated at step 370. At step 380, the alert is displayed on a clinician device, such as clinical user device 226. If at step 360, it is determined that the data received from the infusion pump or the first channel matches that of the associated first patient order at step 385, the data from the infusion pump is communicated at step 385. The data received from the infusion pump is communicated to a user device for display. At step 390, an indication from the user verifying the data received from the infusion pump is received and at step 395, the data is transmitted and stored in the patient's electronic medical record.

Turning now to FIG. 4, an illustrative flow diagram 400 is shown of a method for displaying infusion pump status, vital signs for a patient and patient information from the patient's electronic medical record, in accordance with an embodiment of the present invention. At step 410, data is received from an infusion pump connected to a patient. At step 420, vital sign data from a medical device connected to the same patient is received. At step 430, the status of the infusion pump is determined. For example, device status component 238 may determine whether a device is connected, has been stopped, and/or the rate and volume of the current infusion.

At step 440, the patient's electronic medical record is accessed for patient information. At step 450, the infusion pump status, vital sign information received and patient information from the EMR are displayed simultaneously on a graphical user interface such as the graphical user interface shown in FIG. 8 which will be described in more detail below.

Referring next to FIG. 5, an illustrative flow diagram 500 is shown as a method for displaying infusion data for a first and second patient simultaneously. Initially, data from a first infusion pump for a first patient is received at step 510. The data may include such information as rate of infusion, volume infused, and volume remaining. The data may further include alerts regarding the infusion pump data. At step 520, data is received from a second infusion pump for a second patient. The second patient is different from the first patient. The first infusion pump has been previously associated with a first order for the first patient as described in FIG. 3. The second infusion pump has been associated with an order for the second patient, again, as described in FIG. 3.

At step 530, the patient's electronic medical record for the first and second patient is accessed for patient information. At step 540, infusion data for the first and second patient is displayed simultaneously in a graphical user interface such as that shown in FIG. 11 and will be discussed in further detail below.

Figure 6:
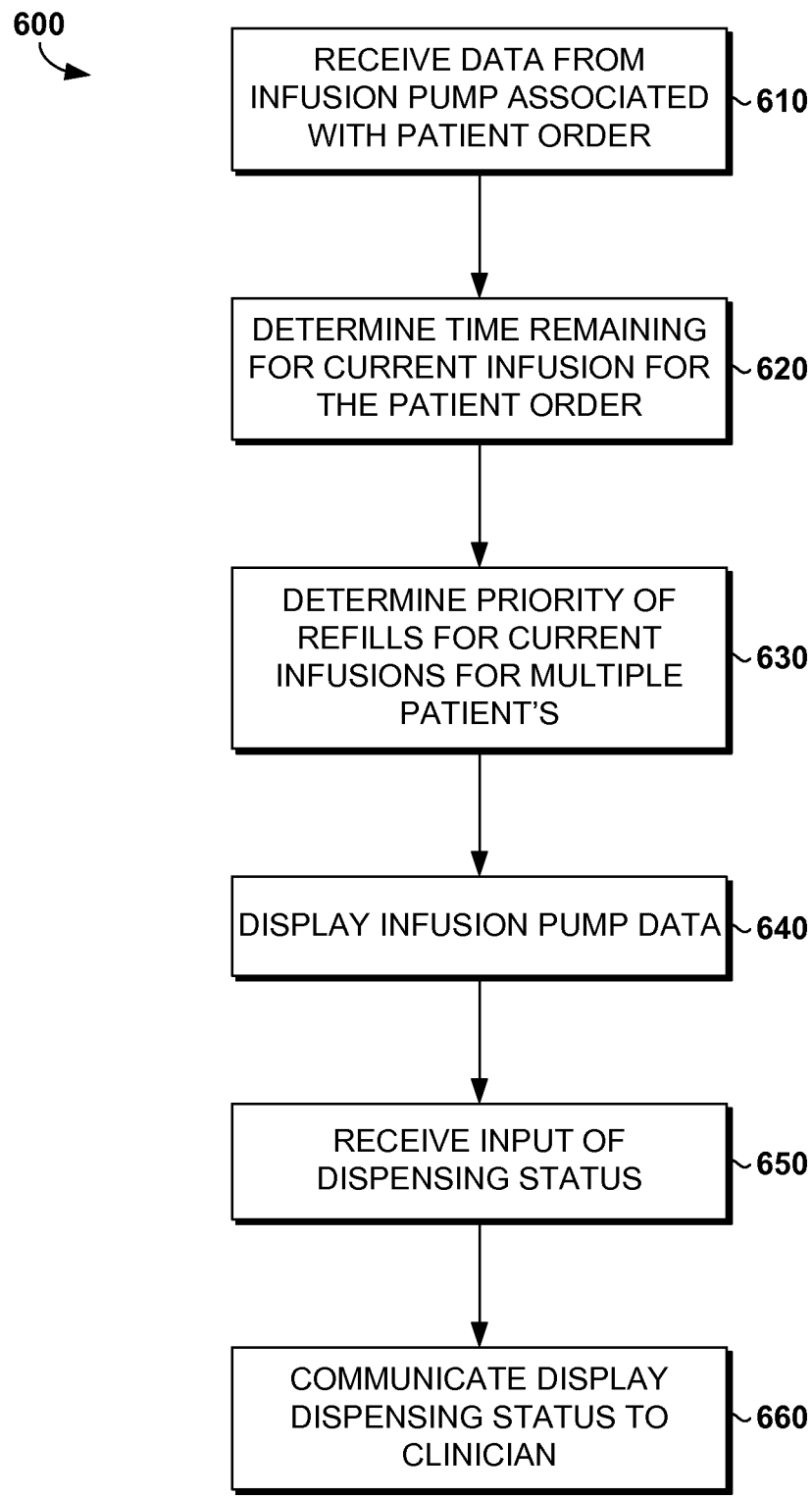

Referring next to FIG. 6, an illustrative flow diagram 600 is shown of a method for receiving input of dispensing status from a pharmacy application and communicating the dispensing status to a clinician. Initially, at step 610, data is received from an infusion pump that has been associated with a patient order. At step 620, the time remaining for the current infusion for the patient order is determined. The time remaining for the current infusion may be determined by the infusion time determining component 242. As described above, a variety of information may be utilized to determine the time remaining infusion fluid to be infused. The information used may include the rates that the rate of infusion, the remaining volume, expiration time of the infusion fluid and the like.

At step 630, the priority of pharmacy refills for current infusion for multiple patients is determined as described above with respect to pharmacy time remaining component 242. The priority of refills in the pharmacy can be determined by the time remaining for the current infusion, the lead time to prepare a replacement infusion, and the number of infusion fluid containers for the particular type of infusion that have already been completed and are in inventory.

At step 640, the infusion pump data received for multiple patients is displayed to a pharmacist. The infusion pump data may be displayed in priority of the highest priority to be completed to the lowest priority to be completed. An exemplary graphical user interface of a multiple patient infusion data view in the pharmacy is shown in FIG. 13.

Turning now to FIG. 7, an illustrative graphical user interface 700 is shown for a patient and plurality of orders and infusion pumps, in accordance with an embodiment of the present invention. Different channels of a multi-channel infusion pumps are capable of being associated with orders for a patient. An exemplary order 715 may be given to a patient of 1000 mL of dextrose 5% with 0.3% NaCl. The type of order may vary depending on the type of infusion pump that is required to carry out the order.

A patient identification area 705 identifies the patient, and gives other information regarding the patient, such as patient name, birth date, gender, age, and the like. An infusion pump channel identification area 710 identifies a channel of an infusion pump, and may also provide information about the channel and the infusion pump. In this example there are two channels 710 and 720 for a single infusion pump. There is one connected channel 710 associated with an order 715 for the patient. There is one channel 720 that has not been associated with an order. There is one medication order 725 that has not been associated with a channel of an infusion pump. Channels 710 and 720 each have a checkbox which may be selected to associate or disassociate a channel of an infusion pump. If an order is not currently associated, it may be selected to be associated with a suggested order. For example, channel 2 of device 1 720 may be associated with the propofol 725 medication order. The checkbox for channel 2 of device 1 720 and the propofol order 725 may be selected and associated by selecting associate button 730. Channel 1 of device 1 710 may be selected to disassociate it from the associated order 715. This may be done by selecting disassociate button 735. If there is an association made between an order and a channel of an infusion pump, the start and end time will be kept in the system for the patient, and most or all inaccuracies will disappear.

FIG. 8 is an illustrative graphical user interface 800 showing infusion data for a selected patient, in accordance with an embodiment of the present invention. A patient identification area 805 allows for the identification of a patient including, but not limited to, the patient's name, date of birth, gender, age, and an identification number or code. Infusion status area 805 indicates the connected infusion pump and channels. Here, there are five infusion pumps and channels connected that have been associated with orders for the patient. Associated orders include dopamine 810, insulin 815, norepinephrine 820, milrinone 825, and propofol 830. Information for each order includes the order information, the current rate of the infusion pump for the order, and any dispensing information. Each order further has an icon indicating the volume remaining for the infusion. Graphical user interface 800 further includes vital signs areas 835 and 840 for respiratory and blood pressure, respectively. In addition, infusion graphing area 860 includes infused volumes over time of milrinone 845, norepinephrine 850, and dopamine 855.

FIG. 9 is an illustrative graphical user interface 900 of a dialogue box indicating that an order currently associated to a pump channel does not match the latest version of the order. This type of box may appear if the order compatibility component 239 determines that the order associated with a pump channel is not current. The box indicates that there has been an order modification 905 for a patient. The box includes an alerting icon 910 stating that the most current version of the order has not been associated with the pump channel for the patient. The box includes an area of the currently associated version of the order 915 and the latest version of the order 920. A user, such as a clinician, may select the latest version button to associate the pump channel with the latest version of the order for the patient.

FIG. 10 is a graphical user interface 1000 depicting infusion information for multiple patients. In the exemplary graphical user interface multiple patient infusion information is included for Unit No. 1 1005. The graphical user interface includes patient identifying information 1010 and associated infusion orders that have been associated with infusion pumps and/or channels 1115. The graphical user interface also includes alerting icons 1120 depicting which patients have infusion alerts.

Figure 11:
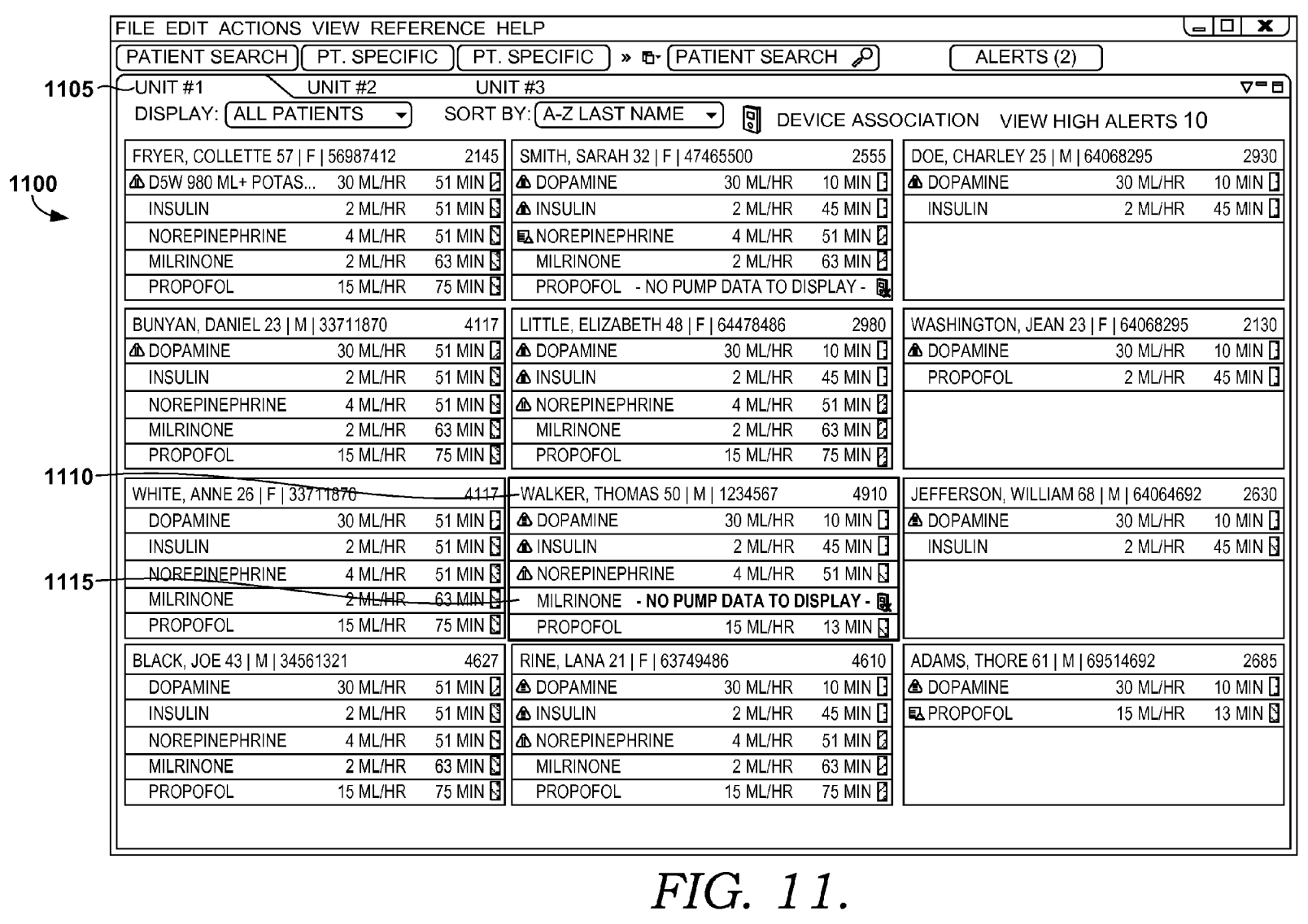

Turning to FIG. 11, graphical user interface 1100 depicting multiple patients for Unit 1 1105 is shown. The multi-unit view shows that patient Thomas Walker 1110 has an associated infusion pump or channel 1115 that currently is not communicating any data. As such, it is displayed that the pump for the particular order has no data to display.

Figure 12:
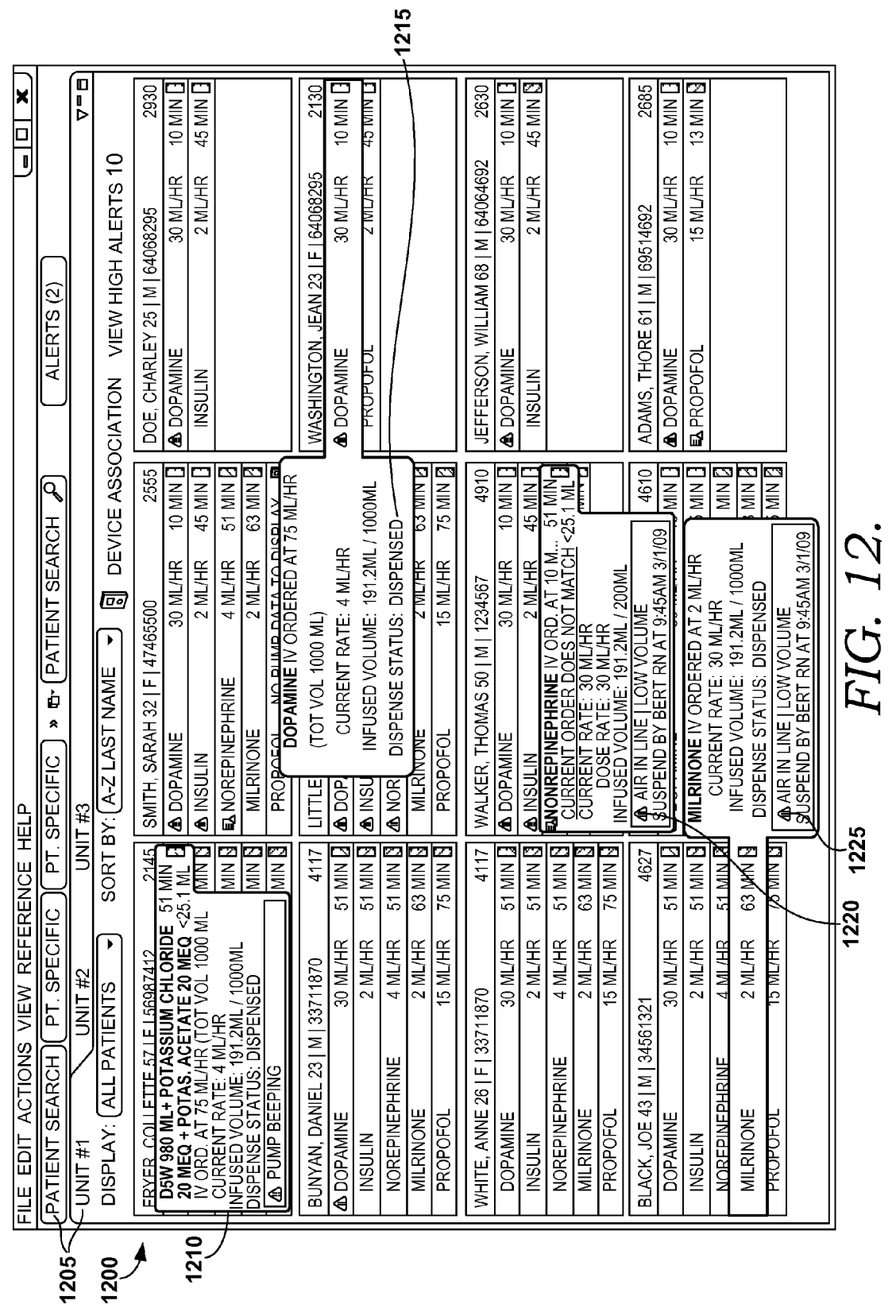

Turning to FIG. 12, an illustrative graphical user interface 1200 of a multi-patient view of infusion data is shown. Again, multiple patients for Unit 1 1205 and their infusion data are shown. In addition, alerts and additional information regarding the alerts are depicted. When a user hovers over an order listed for a patient or alert icon, an additional box appears with more information regarding the order and the alert. For example, box 1210 shows that the pump associated with patient Collette Fryer's potassium chloride order is beeping. The additional information box 1210 also includes the current rates of the infusion, the amount of volume that has been infused, and the dispensing status, along with details of the original order. Textbox 1215 displays details for the dopamine order for patient Jean Washington. It also includes the current rate of infusion received from the infusion pump, along with the volume that has been infused. The textbox also includes the dispensing status from the pharmacy regarding whether a new bag or container of infusion fluid has been dispensed.

Box 1220 depicts that the pump associated with the norepinephrine order for Thomas Walker is sending an alert that there is air in the line of the pump. Further, it shows that this alert has been suspended by a nurse who has gone to examine the pump. It includes the time of suspension of the alert by the nurse. Box 1225 also shows an alert depicting that there is air in the line of the infusion pump associated with the milrinone order. To prevent the pharmacist or automated pharmacy system from duplicating the replace/refill of the infusion. Automated pharmacy system may automatically update the dispense status.

Referring next to FIG. 13, an illustrative graphical user interface 1300 is shown of a pharmacy view of infusion data received from infusion pumps. The interface 1300 includes various types of information relating to multiple devices and channels for multiple patients in health care facility. The types of information include the patient name or identification number, the patient location 1315, the ingredient of the infusion order 1320, the type of infusion 1325, the total volume to be infused for the order 1330, the rate of infusion received from the infusion pump 1335, the amount of fluid of the order that has been infused 1340, the amount of fluid remaining to be infused 1345, and the calculated time remaining of the infusion 1350. Further, alerts 1310 received from the infusion pump indicating that the volume is low or some other type of alert are displayed. In addition, an interactive area regarding the dispensing status 1355 of a replacement or refill for an infusion order is provided. In addition, if a clinician or nurse has placed a request for a refill from a clinician device, this may also be displayed to the pharmacists to prevent the pharmacist or automated pharmacy system from duplicating the replace/refill of the infusion.

A pharmacist or technician in the pharmacy may indicate the status of the replacement or refill of infusion fluid. These statuses include that the replacement infusion has been delivered 1375, that the delivery is in process 1380, the infusion has been dispensed but yet to begin delivery 1385, that the dispensing is in process 1390 or the replacement/refill infusion is being prepared. In some instances, such with an automatic pharmacy dispensing system, the status of the replacement or refill infusion can be updated automatically upon dispensing. This indication allows for pharmacy users to know the status of infusion orders to be filled by the pharmacy and adjust the workflow accordingly. In other words, if an infusion replacement has been dispensed or delivered, there is no need for another technician to fulfill the order. However, if no status is indicated, then the pharmacy user knows to begin dispensing.

That replacement/refill infusion status indication for a patient order can be communicated to a clinician, such as a nurse. This allows the nurse to see the status of the replacement/refill of the pharmacy without having to directly contact the pharmacy to check status.

The pharmacy infusion orders for the patients are displayed in order of time remaining for the existing infusion. For example, patients with the lowest calculated time remaining for their current infusion are displayed at the top of the graphical user interface 1300 and patients with the most calculated time remaining for need of a replacement infusion are displayed at the bottom. Icons indicating that the rates of an infusion are increasing 1365 or decreasing 1370 are also displayed so that a pharmacist can see if a particular infusion may need to be replaced sooner than the calculated time remaining for the current infusion.

Many different arrangements of the various components depicted, as well as components not shown, are possible without departing from the scope of the claims below. Embodiments of our technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

The invention claimed is:

1. A method for providing an alert indicating that an operation of an infusion pump is not consistent with an order, which specifies an infusion to be administered to a patient, the method comprising:

receiving an identification of the order and an identification of the infusion pump, wherein the order specifies an order infusion rate at which a fluid is to be administered to the patient;

storing an association of the order and the infusion pump to one another, wherein the association is maintained by a processing unit separate from the infusion pump;

receiving by the processing unit a continuous data feed from the infusion pump, the continuous data feed including a volume of the fluid that has been administered by the infusion pump over a time duration;

based on the volume of the fluid and the time duration, calculating an infusion rate indicating a rate at which the infusion pump has been administering the fluid;

comparing the infusion rate that was calculated to the order infusion rate to determine that the infusion rate and the order infusion rate are not consistent;

retrieving an updated infusion order that is associated with the patient and that is not associated with the infusion pump;

transmitting an alert to a mobile computing device notifying a recipient that the infusion rate and the order infusion rate are not consistent, wherein the alert includes a selectable indication of the updated infusion order;

receiving from the mobile computing device a selection of the selectable indication; and updating the association to include the updated infusion order.

2. The method of claim 1, further comprising:

storing the association of the updated infusion order and the infusion pump in an electronic medical record for the patient.

* * * * *